(12) United States Patent
Hong et al.

(10) Patent No.: US 10,519,203 B2
(45) Date of Patent: Dec. 31, 2019

(54) GENE FOR BIOSYNTHESIS OF CORE STRUCTURE OF OPHIOBOLIN

(71) Applicant: WUHAN UNIVERSITY, Wuhan (CN)

(72) Inventors: Kui Hong, Wuhan (CN); Huiying Meng, Wuhan (CN); Hangzhen Chai, Wuhan (CN); Ru Yin, Wuhan (CN); Zixin Deng, Wuhan (CN)

(73) Assignee: WUHAN UNIVERSITY, Wuhan (CN)

( * ) Notice: Subject to any disclaimer, the term of this patent is extended or adjusted under 35 U.S.C. 154(b) by 0 days.

(21) Appl. No.: 15/712,172

(22) Filed: Sep. 22, 2017

(65) Prior Publication Data

US 2018/0009855 A1     Jan. 11, 2018

Related U.S. Application Data

(63) Continuation-in-part of application No. PCT/CN2016/076822, filed on Mar. 21, 2016.

(30) Foreign Application Priority Data

Mar. 24, 2015 (CN) .......................... 2015 1 0130163

(51) Int. Cl.
    *C12N 9/10*          (2006.01)
    *C12P 7/02*          (2006.01)
    *C07K 14/38*        (2006.01)

(52) U.S. Cl.
CPC ............... *C07K 14/38* (2013.01); *C12N 9/10* (2013.01); *C12N 9/1085* (2013.01); *C12P 7/02* (2013.01)

(58) Field of Classification Search
None
See application file for complete search history.

(56) References Cited

U.S. PATENT DOCUMENTS 8,288,149 B2 * 10/2012 Bailey .................... C12N 15/80
                                                             435/255.1

FOREIGN PATENT DOCUMENTS

CN            104673813 A      6/2015

OTHER PUBLICATIONS

M. Orsenigo, Estrazione e purificazione della cochliobolina, una tossina prodotta da Helminthosporium oryzae, Phytopathologische Zeitschrift, 1957, pp. 189-196, vol. 29, Blackwell Publishing, United States.
C. L. Tipton et al., The effect of ophiobolin A on glucose uptake by animal cells, Nutrition Reports International, Apr. 1981, pp. 723-727, vol. 23, No. 4, Elsevier, United States.
T. Yang et al., The novel agent ophiobolin O induces apoptosis and cell cycle arrest of MCF-7 cells through activation of MAPK signaling pathways, Bioorganic & Medicinal Chemistry Letters, 2012, pp. 579-585, No. 22, Elsevier Ltd., United States.
W. Sun et al, Ophiobolin-O reverses adriamycin resistance via cell cycle arrest and apoptosis sensitization in adriamycin-resistant human breast carcinoma (MCF-7/ADR) cells, Marine Drugs, 2013, pp. 4570-4584, vol. 11, MDPI AG, Basel, Switzerland.
K. Tsuna et al., Enantioselective total synthesis of (+)-ophiobolin A, Chemistry—A European Journal, 2013, pp. 5476-5486, vol. 19, Wiley-VCH, Weinheim, Germany.
K. Li et al., Construction of the basic skeleton of ophiobolin A and variecolin, Organic & Biomolecular Chemistry, 2013, pp. 7550-7558, vol. 11, Royal Society of Chemistry, United Kingdom.
L. Canonica et al., The biosynthesis of ophiobolins, Tetrahedron Letters, 1967, p. 3371, No. 35, Elsevier, United Kingdom.
S. Nozoe et al., Biosynthesis of ophiobolins from the doubly labeled mevalonates (1), Tetrahedron Letters, 1968, p. 2347, vol. 9, Issue 19, Elsevier, United Kingdom.
S. Nozoe et al., Enzymic formation of a tricyclic sesterterpene alcohol from mevalonic acid and all-trans-Geranylfarnesyl pyrophosphate, Chemical Communications, 1969, pp. 1319-1320, Royal Society of Chemistry, United Kingdom.
R. Chiba et al., Identification of ophiobolin F synthase by a genome mining approach: A sesterterpene synthase from Aspergillus clavatus, Organic Letters, Feb. 1, 2013, pp. 594-597, vol. 15, No. 3, American Chemical Society, United States.
P. Steffen et al., Hypothetical Protein ASPCAL05226 [Aspergillus Calidoustus], GenBank, Jan. 4, 2016, Database accession No. CEL040941, National Center for Biotechnology Information, United States.

* cited by examiner

*Primary Examiner* — Richard G Hutson
(74) *Attorney, Agent, or Firm* — Matthias Scholl P.C.; Matthias Scholl

(57) ABSTRACT

A gene for biosynthesis of core structure of ophiobolin, the gene being the AuOS gene of *Aspergillus* sp. 094102, deposited with the accession number CCTCC No: M208153, the gene sequence thereof being shown as SEQ ID NO. 1. Also provided is a method of preparation of ophiobolin using the gene.

5 Claims, 12 Drawing Sheets

Specification includes a Sequence Listing.

FIG. 2

GENE FOR BIOSYNTHESIS OF CORE STRUCTURE OF OPHIOBOLIN

CROSS-REFERENCE TO RELATED APPLICATIONS

This application is a continuation-in-part of International Patent Application No. PCT/CN2016/076822 with an international filing date of Mar. 21, 2016, designating the United States, now pending, and further claims foreign priority to Chinese Patent Application No. 201510130163.6 filed Mar. 24, 2015. The contents of all of the aforementioned applications, including any intervening amendments thereto, are incorporated herein by reference. Inquiries from the public to applicants or assignees concerning this document or the related applications should be directed to: Matthias Scholl P. C., Attn.: Dr. Matthias Scholl Esq., 245 First Street, 18th Floor, and Cambridge, Mass. 02142.

BACKGROUND OF THE INVENTION

Field of the Invention

This invention relates to the field of genetic engineering, and more particularly to a gene for biosynthesis of the core structure of ophiobolin from *Aspergillus* sp. 094102, and to methods of making and using the same.

Description of the Related Art

Ophiobolins are sesterterpenes. They are characterized by a C5-C8-C5 ring core structure (FIG. 1). They include ophiobolin A, C, F, H, M, L, O, Q, R, and S. The compounds show antimicrobial activity and activity against nematodes and viruses, as well as on various tumor cell lines which show significant cytotoxicity.

Because ophiobolins present extensive and important biological targets, they have attracted attention in terms of improving their production yield and studying mechanisms of reactions used to synthesize them. Beginning in 1992, chemical syntheses of ophiobolins and their derivatives have been reported, but the complex structure of ophiobiolins still makes their synthesis very challenging. The total synthesis of the ophiobolin A has been completed, but the synthetic steps are difficult to carry out.

Known ophiobolins all contain a C5-C8-C5 ring, but the olefinic bond number and location are not the same, such as in the case of ophiobolin E which contains two more olefinic bonds than ophiobolin F, particularly at C10-14 and at C12-13. This suggests that the ring formation mechanism may not be the same for the various ophiobolins. Therefore, it is necessary to undertake an in-depth systemic study of the cyclization mechanism, and to develop further synthetic method to produce ophiobolin derivatives and proteins that are associated with the same.

SUMMARY OF THE INVENTION

In view of the above-described problems, it is one objective of the invention to provide a biosynthesis gene for ophiobolin compound core structure. Another objective of the present disclosure is to provide the application of the gene.

The objectives of the invention are achieved through the following technical solutions:

An ophiobolin core structure biosynthesis gene, the AuOS, was cloned from *Aspergillus* sp. 094102 that has been deposited in China Center for Type Culture Collection (CCTCC) under the Budapest Treaty with an accession number CCTCC No: M208153 and that has been made available to the public. Its gene sequence is shown as SEQ ID NO. 1. The aforementioned AuOS contains 3 introns. The cDNA is 2178 bp, as shown in the sequence (SEQ ID NO. 2). The stated ophiobolins including series compounds of those featured a C5-C8-05 ring core structure, such as ophiobolin K, 6-epi-ophiobolin K, ophiobolin G, 6-epi-ophiobolin G, 6-epi-ophiobolin Q, ophiobolin U, 6-epi-ophiobolin V, and ophiobolin W, etc.

The stated protein coded by AuOS gene is named as AuOS. Its amino acid sequence is shown in SEQ ID NO. 3. AuOS protein contains two domains, including 324 N-terminal amino acids of terpene synthase domain and 401 C-terminal amino acids of E-IPPS (Trans isopentene pyrophosphate synthase) domains. Among them, the terpene synthase domain contains two conserved motifs of DDEID and NDLFSYEKE, which are for recognizing $Mg^{2+}$ and substrate. E-IPPS domain also contains two conserved characteristic motifs DDIED and DDYQN, which are of similar functions. AuOS protein of the present disclosure can be expressed in various systems (such as all prokaryotic expression system of *Escherichia coli* and *Streptomyces*, and all eukaryotic expression system such as *Pichia* spp., *Saccharomyces cerevisiae* and *Aspergillus oryzae*). And while AuOS protein can be purified by using a variety of methods (such as nickel affinity chromatography). Abovementioned AuOS protein has both chain elongation and terpene cyclase functions. AuOS protein can use four species of compounds: DMAPP (dimethylallyl diphosphate), GPP (geranyl diphosphate), FPP (farnesyl diphosphate), and GGPP (geranylgeranyl diphosphate), respectively, with added IPP (isopentenyl diphosphate), directly synthesis the core structure of ophiobolin compounds.

Based on abovementioned function of AuOS as both chain length elongation and terpene cyclizaiton, AuOS gene not only can be applied for further clarifying the biological synthetic pathway of ophiobolin, and also helps the enzymatic investigation. While AuOS protein can catalyze the synthesis of core structure of ophiobolin, with further modification such as oxidation-reduction to produce series ophiobolin compounds and also benefit for the increase of production yield.

This invention firstly discovered the AuOS gene from *Aspergillus* sp. 094102. Its encoding protein can catalyze DMAPP on de novel biosynthesis of ophiobolin core structure. This invention provides opportunities of biosynthesis ophiobolin core structure in vitro, or using the genetic engineering approach. In addition, the core structure can be modified through chemical or biological ways to produce series molecules which have important medicinal value.

BRIEF DESCRIPTION OF THE DRAWINGS

FIG. 2 is an alignment of amino acid sequences of AuOS from *Aspergillus* sp. 094102 and AcOS from *Aspergillus clavatus* NRRL1.

DETAILED DESCRIPTION OF THE EMBODIMENTS

Figure 1:
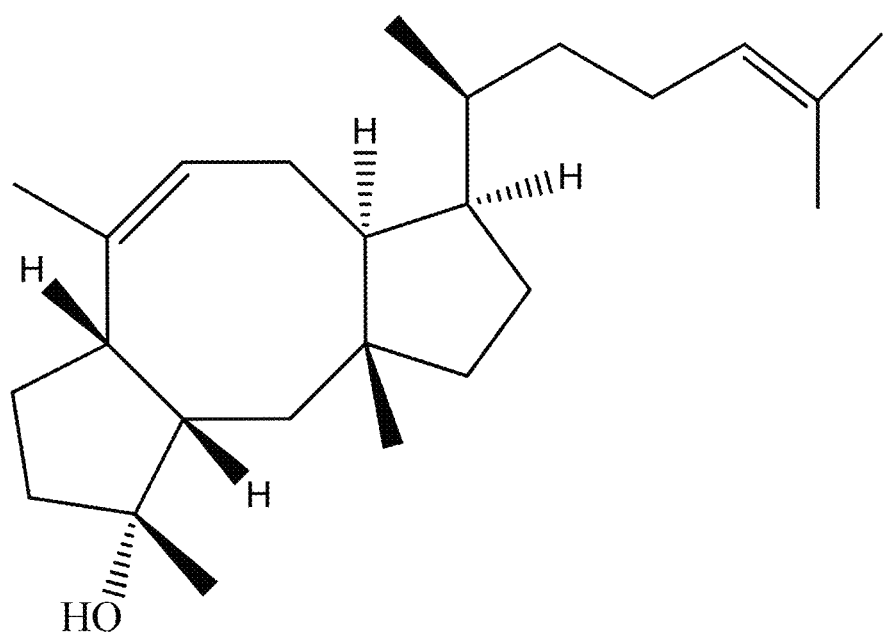
FIG. 1 shows core structure of ophiobolin.

Further detailed descriptions of the present disclosure are described below with specific embodiments. The embodiments are used only to illustrate the invention but not limit the scope of the invention.

Figure 2:
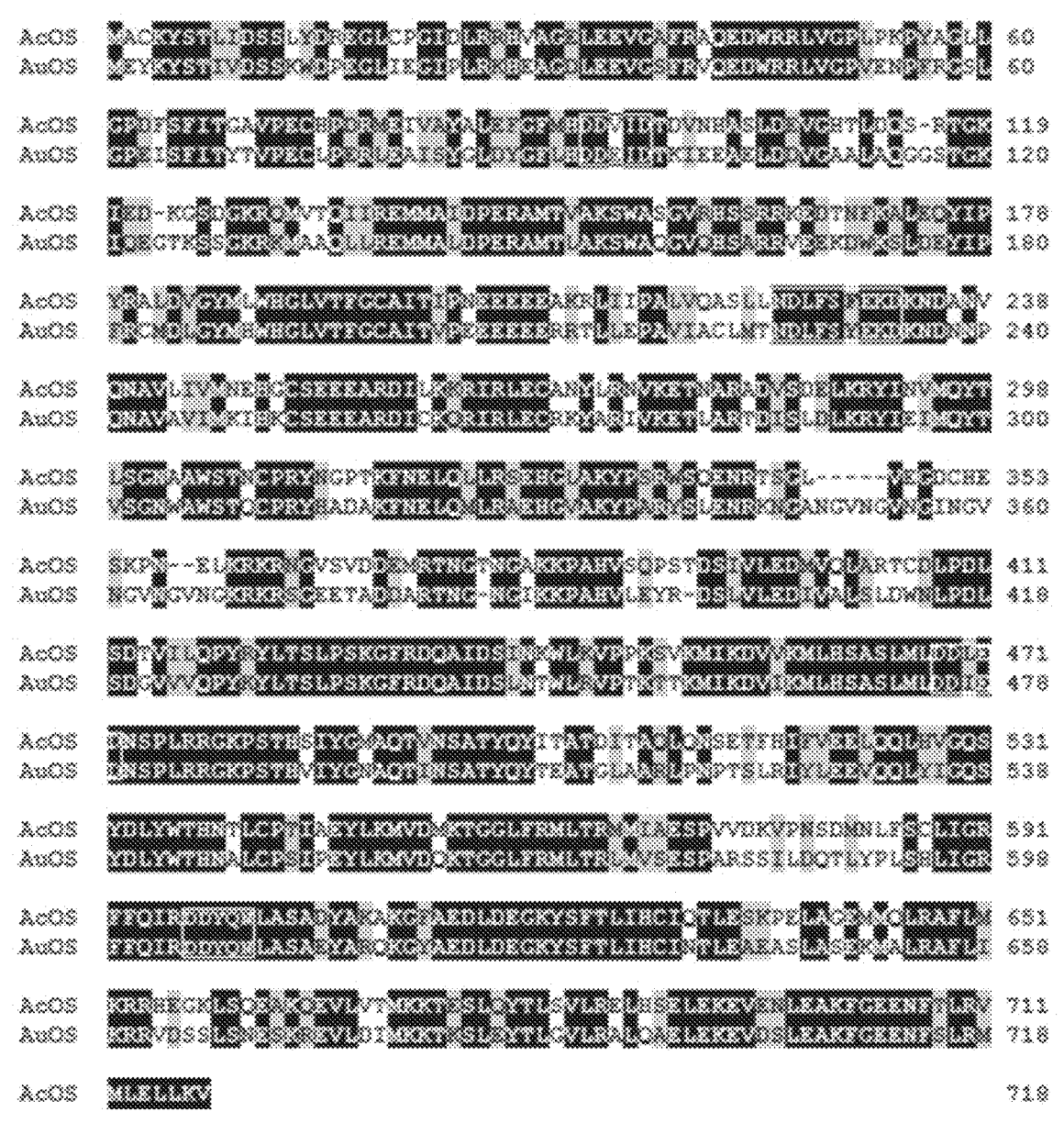

The ophiobolin core structure biosynthesis gene provided by the invention, named AuOS, was cloned from *Aspergillus* sp. 094102. Its gene sequence is shown as SEQ ID NO. 1. The AuOS contains 3 introns. The cDNA size is 2178 bp. Its sequence is shown in the SEQ ID NO. 2. The protein coded by AuOS gene is named as AuOS. Its amino acid sequence is shown in SEQ ID NO. 3 Homologous sequences of AuOS protein from *Aspergillus* sp. 094102 were searched from a public database and aligned, which indicated that AuOS was highly matched to protein AcOS (*A. clavatus* NRRL 1 ophiobolin F synthesis), with the identity of 65% (*Aspergillus clavatus* NRRL 1) (Ryota Chiba, Atsushi Minami, Katsuya Gomi, et al. Identification of ophiobolin F synthase by a genome mining approach: a sesterterpene synthase from *Aspergillus clavatus*. Organic Letters. 2013, 15 (3), 594-597). AcOS is a chimera terpene synthase. It contains two domains, including 324 amino acids of terpene synthase domain at N-terminal and 401 amino acids of E-IPPS (Trans isopentene pyrophosphate synthase) domains at C-terminal. These two domains are crucial for the catalytic function. Among them, the terpene synthase domain contains two conserved motifs of DDEID and NDLFSYEKE, which are used to recognizing $Mg^{2+}$ and substrate. The E-IPPS domain also contains two conserved characteristic motifs of DDIED and DDYQN, which are of similar functions (FIG. 2).

Example 1 AuOS Gene Cloning

1. RNA extraction from strain *Aspergillus* sp. 094102.

Extraction of the total RNA from mycelia of *Aspergillus* sp. 094102 was carried with the German company QIAGEN RNeasy Mini Kit (50) Kit (stock #74104), do as the following:

(1) Estimate the amount of mycelial samples. Bisicly takes 50 mg of hyphae at one time for micro extraction.

(2) Ground the sample into a powder with liquid nitrogen, transferred to 1.5 mL plastic centrifuge tubes.

(3) Add 450 μL Buffer RLT (Lysis buffer) in the centrifugal tube (Add 10 μL β-mercaptoethanol per 1 mL Buffer RLT before use), oscillations on the oscillator 1-3 min (solution at the bottom of the tube must be oscillated).

(4) Centrifuge for 2 min at 4° C. 13000×g, transfer the supernatant to a clean 1.5 mL plastic centrifugal tube (middle-phase and lower organic phase containing DNA, proteins and other impurities, avoid touching or drawing).

(5) Add 0.5 volume of anhydrous ethanol, fully reverse the mix till thoroughly mixed.

(6) Transfer this solution to a centrifugal adsorption column and centrifuge at 4° C. 8000×g for 15 s, discard penetrate liquid.

(7) Add 700 μL Buffer RW1 (wash buffer) into centrifugal adsorption column and centrifuge at 4° C. 8000×g for 15 s, discard penetrate liquid.

(8) Move the centrifugal column to a new collection tube (no RNA enzymes), add 500 μL Buffer RPE (wash buffer) and centrifuge at 4° C. 8000×g for 15 s, discard penetrate liquid.

(9) Add 500 μL Buffer RPE (wash buffer, add 4 times volume of ethanol before use). Centrifuge for 2 min at 4° C. 13000×g.

(10) Move the centrifugal column to a new collection tube (no RNA enzymes). Centrifuge for 2 min at 4° C. 13000×g

(11) Move the centrifugal column to a new 1.5 mL plastic centrifugal tube (no RNA enzymes), add 30-50 μL RNase-free water, centrifuge at 4° C. 8000×g for 15 s. Solution in centrifugal tube is RNA samples of DNA free.

(12) Transfer 40 μL RNA sample to a new 1.5 mL plastic centrifugal tube (no RNA enzymes), add 5 μL each of DNase I and DNase I buffer, incubated at 37° C. for 2 h.

(13) Add 5 μL of 50 mM EDTA, incubated at 65° C. for 10 min, preserved at −80° C.

2. Reverse Transcription

America's Revert of Thermo Fisher Scientific Company Aid First strand cDNA synthesis Kit (model K1621) was used for reverse transcription, the steps are as follows:

(1) Take 2 μg of the prepared RNA samples, add 1 μL of 10 μM Oligo (dT) 18, add RNase-free water up to 12 μL, incubated at 65° C. for 5 mM, cool for 5 mM with ice, centrifuge at 4° C. 13000×g for 2 mM.

(2) Add 4 μL of 5×reaction buffer, 1 μL of Ribo Lock RNase Inhibitor, 1 μL of RevertAid RT, 2 μL of 10 mM dNTP Mix, and RNase-free water up to 20 μL. incubated at 42° C. for 60 min, then at 70° C. for 5 min.

3. Applificaiton of AuOS Gene

According to the genomic sequence of *Aspergillus* sp. 094102, the primer pair was designed as following:

```
Forward primer (AuOS-F):
                                    (SEQ ID NO. 4)
5'-CATATGATGGAGTATAAGTACTCGACC-3'
(contain a restriction enzyme recognition site
of Nde I to construct the expression vector);

Reverse primer (AuOS-R):
                                    (SEQ ID NO. 5)
5'-AAGCTT TCAAACCTTCAGCAGCTCCA-3'
(contain a restriction enzyme recognition site
of Hind III to construct the expression vector).
```

Reaction system: 1 μL of Pfu DNA polymerase (New England Biolabs, USA), 21 μL of sterilized deionized water, 1 μL of Pfu DNA polymerase 5×NF buffer, 2.5 μL (10 μM) each of forward and reverse primer, and 2 μL of cDNA template.

PCR amplification conditions: initial denaturation at 95° C. for 3 min; denaturation at 95° C. for 30 s; anneal at 53° C. for 20 s, elongation at 72° C. for 70 s, cycle for 35 times; elongation at 72° C. for 10 min.

4. Recovery of Target DNA

After the electrophoresis of the PCR product, the target DNA was recovered from the agarose gel according to the Gel Extraction Kit (100) (Series No. D2500-01) supplier (OMEGA, Germany) as following:

(1) Agarose gel electrophoresis for target DNA using 1% agarose gel with trihydroxymethyl aminomethane-acetic acid (abbreviated as TAE) buffer solution.

(2) Cut the target DNA fragment under UV light from the agarose gel (at this point, part of the gel without target DNA should be removed to minimize gel size and improve DNA recovery, using paper towels absorb liquid on the surface of the gel).

(3) Chop the gel block to increase the gel melting time and improve DNA recovery.

(4) Weigh the gel block and calculate its size. Add binding buffer at the ratio of 400 μL per 100 mg agarose gel, incubate at 50-60° C. for 10 min (mix every 2 min till all the gel melt).

(5) Melt gel solution and transfer to the collection tube with adsorption column, centrifuge at 4° C. 10000×g for 15 s, discard liquid.

(6) Add 500 μL XP2 (Binding buffer) to the adsorption column, centrifuge at room temperature, 10000×g for 1 min, discard liquid.

(7) Add 700 μL SPW (Wash buffer) to the adsorption column, centrifuge at room temperature, 10000×g for 1 min, discard liquid.

(8) Add 300 μL SPW (Wash buffer) to the adsorption column, centrifuge at room temperature, 10000×g for 1 min, discard liquid.

(9) Centrifuge at room temperature, 10000×g for 2 min with the cover open.

(10) Transfer the adsorption column to a new 1.5 mL tube. Add 30-50 μL elution buffer or sterilized water on the center of the column, keep at room temperature for 2-5 min, centrifuge at room temperature, 10000×g for 1 min.

(11) Check the recovered product with 1% agarose gel electrophoresis.

5. Target DNA Cloning

Recovered DNA was ligated to the pEASY-Blunt vector at 16° C. for 24 h. The resultants were transformed to *Escherichia coli* TOP 10 cells. The positive clones were selected using rapid testing methods after overnight culture, as follows:

(1) Pick out about 20 clones from the transformation plate with a sterile toothpick, streak onto the LA plates containing benzyl ammonia resistant (100 μg/mL) plate, incubat at 37° C. for 8 h.

(2) Add 30 μL STE solution (20 mM Tris-HCl, 25 mM EDTA, 75 mM NaCl) in 1.5 mL plastic centrifugal tube, transfer the single colony individually to the plastic centrifugal tubes with toothpick, vortex 2 min till mixed well.

(3) Add equal volume of chloroform:phenol:isoamyl alcohol (v:v:v=24:25:1), after the shake mix, centrifuge at room temperature 10000×g for 5 min.

(4) Check the Supernatant using 1% agarose gel electrophoresis, to determine initially whether the plasmid containing the inserted exogenous fragments.

The plasmid containing small foreign fragment were extracted using plasmid extraction kits (Wuhan Maikelaibo technology, Ltd). The procedure is as following:

(1) Transfer the single colony to ampicillin (100 μg/mL) resistant LB medium incubated at 37° C. 220 rpm, overnight, and then transfer 2 mL to 2 mL plastic centrifugal tube, centrifuge at room temperature, 10000×g for 1 min, discard liquid.

(2) Add 250 μL Buffer 1, vortex to make the cells suspend thoroughly.

(3) Add 250 μL Buffer 2, invert the centrifuge tube 5-6 times mildly, till the solution turned to clear.

(4) Add 350 μL Buffer 3, invert the centrifugal tube 3-5 times mildly to mix thoroughly.

(5) Centrifuge at room temperature 12000×g for 10 min. Transfer the supernatant carefully into the collection tube adsorption column. Centrifuge at 12000×g, for 1 min at room temperature. Pour the liquid out of the collection tube. Put the column back into the collection tube.

(6) Add 500 μL Buffer D, centrifuge at room temperature, 12000×g, for 1 min. Pour the liquid out of the collection tube, put the column back into the collection tube.

(7) Add 600 μL Buffer W, centrifuge at room temperature, 12000×g, for 1 min. Pour the liquid out of the collection tube, put the column back into the collection tube.

(8) Add 6300 μL Buffer W, centrifuge at room temperature, 12000×g, for 1 min.

(9) Move the column to a clean 1.5 mL plastic centrifuge tube; add 50-100 μL Buffer E to the adsorb film at the center, standing for 1 min at room temperature, centrifuge at room temperature, 12000×g, for 1 min to wash off the cloning plasmid.

The above plasmid was double digested with Nde I and Hind III (American New England Biolabs pfu restriction enzymes) in reaction conditions of following: 2 μL Cutsmart buffer, 0.5 μL Nde I, 0.5 μL Hind III, 1 μL plasmid DNA, and 16 μL ddH$_2$O, at 37° C. for 1 h; then the products was checked with 1% of agarose gel electrophoresis to determine whether the DNA fragment cloned in plasmid is the target DNA fragment. Submit 1 mL of culture contain the cloned plasmid of target DNA to Qingke Company for sequencing to confirmed the target DNA has been successfully cloned without mutation. The recombinant clone was named as pEASY®-Blunt-AuOS.

Example 2 Expression and Purification of AuOS

This procedure including construction of *E. coli* expression vector containing AuOS, heat-induced transformation into *Escherichia coli* BL21 (DE3), and further verify the AuOS gene function.

1 Construction of *E. coli* expression vector containing AuOS.

The target DNA fragment was digested with restriction enzymes Nde I and Hind III from the recombinant plasmid-pEASY-Blunt-AuOS. The pET28a vector was double digested using the same enzymes. Both of the above products were separated using agarose gel electrophoresis. The target gene fragment and pET28a vector were recovered using OMEGA gel extraction Kit. Using T4 DNA ligase, AuOS gene was inserted into the pET28a vector. The products were transformed to *Escherichia coli* TOP 10 cells and *Escherichia coli* recombinant expression vector pET28a-AuOS was obtained through colony quick test and enzyme digestion verification.

2. Expression of AuOS Gene

The recombinant plasmid pET28a-AuOS and pET28a were heat-inducing transformed to *E. coli* BL21 (DE3). The transformed plasmid containing small foreign fragment were extracted using plasmid extraction kits (Wuhan Maikelaibo technology, Ltd) and confirmed by digesting with Nde I and Hind III restriction enzymes. The engineered *E. coli* strains containing recombinant plasmid pET28a-AuOS and pET28a were successfully constructed.

Figure 3:
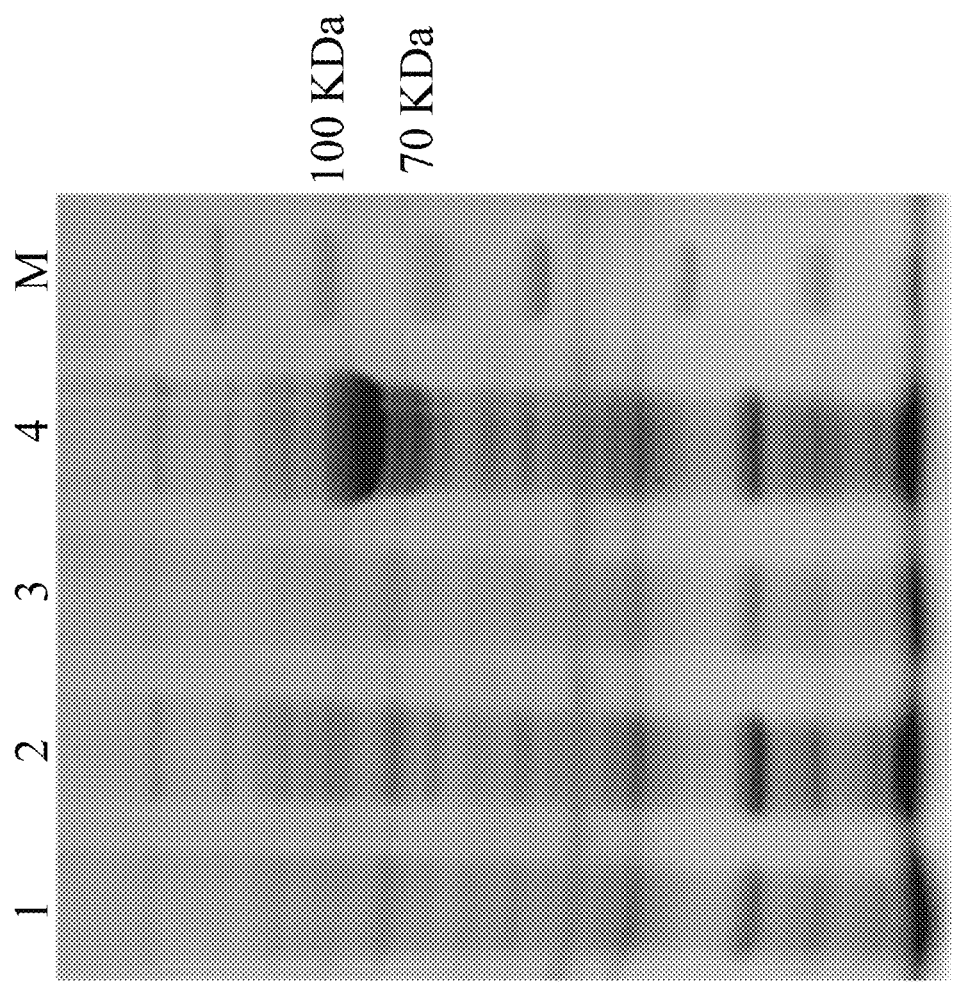
FIG. 3 shows results of AuOS gene expression, 1: pET28a before induction; 2: pET28a after induction; 3: pET28a-AuOS before induction; 4: pET28a-AuOS after induction; M: protein ladder.

The engineered *E. coli* BL21 (DE3) strains containing recombinant plasmid pET28a-AuOS and pET28a are inoculated individually in 5 mL kanamycin (50 μg/mL) resistant LB broth, overnight cultured at 37° C., 220 rpm. Then the fresh cultures are inoculated to another 5 mL kanamycin (50 μg/mL) resistant LB broth with 1% inoculation. Add IPTG to concentration of 1 mM after culturing for 2-3 h and the Moo reaches to 0.4-0.6 at 37° C., continue the inducted culture for 3-5 h (1 mL of culture portion is taken out before the induction). Take 200 μL culture each of before and after induction, add 5×SDS-PAGE buffer and boil for 30 min, centrifuge 12000×g at room temperature for 10 min, check 10 μL of supernatant with SDS-PAGE. The result showed that the target protein is successfully expressed in *E. coli* BL21(DE3) (FIG. 3).

3. Purification of AuOS Protein

Take 5 mL overnight culture of *Escherichia coli* BL21 (DE3) containing recombinant plasmid pET28a-AuOS, inoculate at the ratio of 1% to 500 mL LB medium containing kanamycin (50 μg/mL), cultivate at 37° C., 220 rpm to an OD600 of 0.4-0.6, add IPTG to 1 mM final concentration, induce the culture for 3-5 h at 37° C. Centrifuge at room temperature, 5000 rpm for 5 min, the induced culture of *E. coli* is collected, resuspended in distilled water. Centrifuge at room temperature, 5000 rpm for 5 min, discard the supernatant (repeat twice). Then resuspend the biomass with HEPES buffer, Centrifuge at room temperature, 5000 rpm for 5 min, discard supernatant. Add 10 mL HEPES buffer to the biomass, mix thoroughly and ultra-sonicate on ice (ultrasonicate 5 mS, 5 mS intervel, power 300 W) for 30 min. Then centrifuge at room temperature, 23000 rpm for 20 min, filer the supernatant with 0.45 μm filter membrane for purification. The protein purification method is as following:

(1) Add proper amount of nickel beads matrix onto the column, let the anhydrous ethanol fully flow out of the matrix under the action of gravity.

(2) Wash column with 20 mL aseptic dd$H_2O$.

(3) Balance the column with 20 mL HEPES buffer (4) Add the supernatant containing the target protein to the column, collect the effluent liquid, detect with SDS-PAGE.

(5) Elute with iminazole eluent at concentrations of 2 mM, 5 mM, 25 mM, 50 mM, 100 mM, 200 mM, 300 mM and 500 mM diluted with HEPES buffer. Collect the elution and detect with SDS-PAGE.

Figure 4:
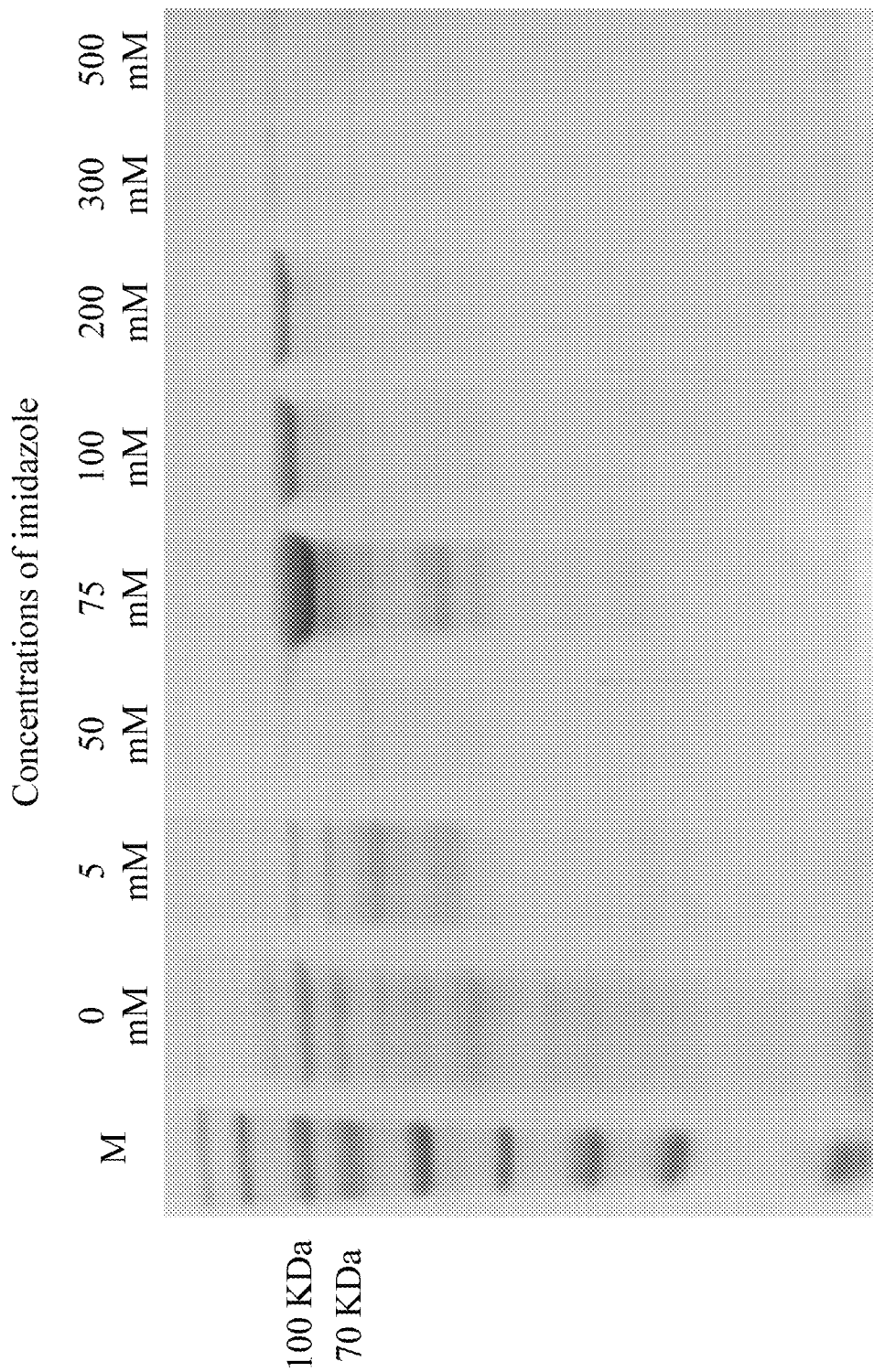
FIG. 4 show result of protein purification after AuOS gene expression. M: protein ladder.

The SDS-PAGE detection results showed that a relatively pure protein (FIG. 4) obtained at 50 mM and 100 mM imidazole elution. The concentrated pure protein 2.5 mL is obtained using 10 kDa ultra-filtration tube. Protein in concentrated solution was desalted with GE Healthcare PD-10 desalting columns (order number 17-0851-01). Detailed steps as following:

(1) Balance the column with 10 mL balance buffer, discard the waste liquids, and repeat 4 times.

(2) Add 2.5 mL protein solution till it soaks fully in the column, discard the waste liquid.

(3) Add 3.5 eluent and collect the elution (this is the desalted protein solution). Deposit at −80° C. for further use.

Example 3 Function Analysis of AuOS

Figure 5:
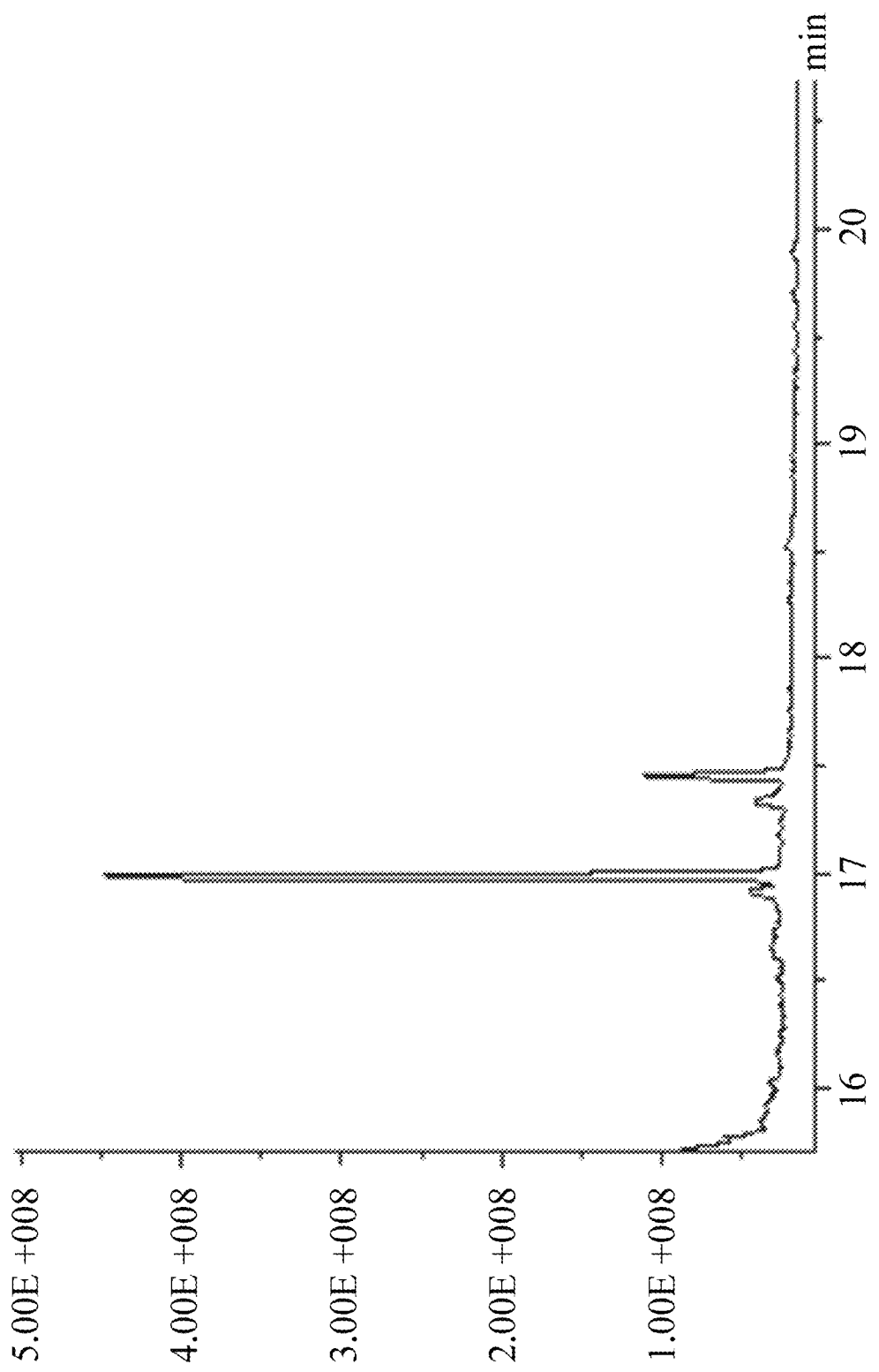
FIG. 5 is a chromatogram of products of in vitro reaction using DMAPP and IPP as substrates.
Figure 6:
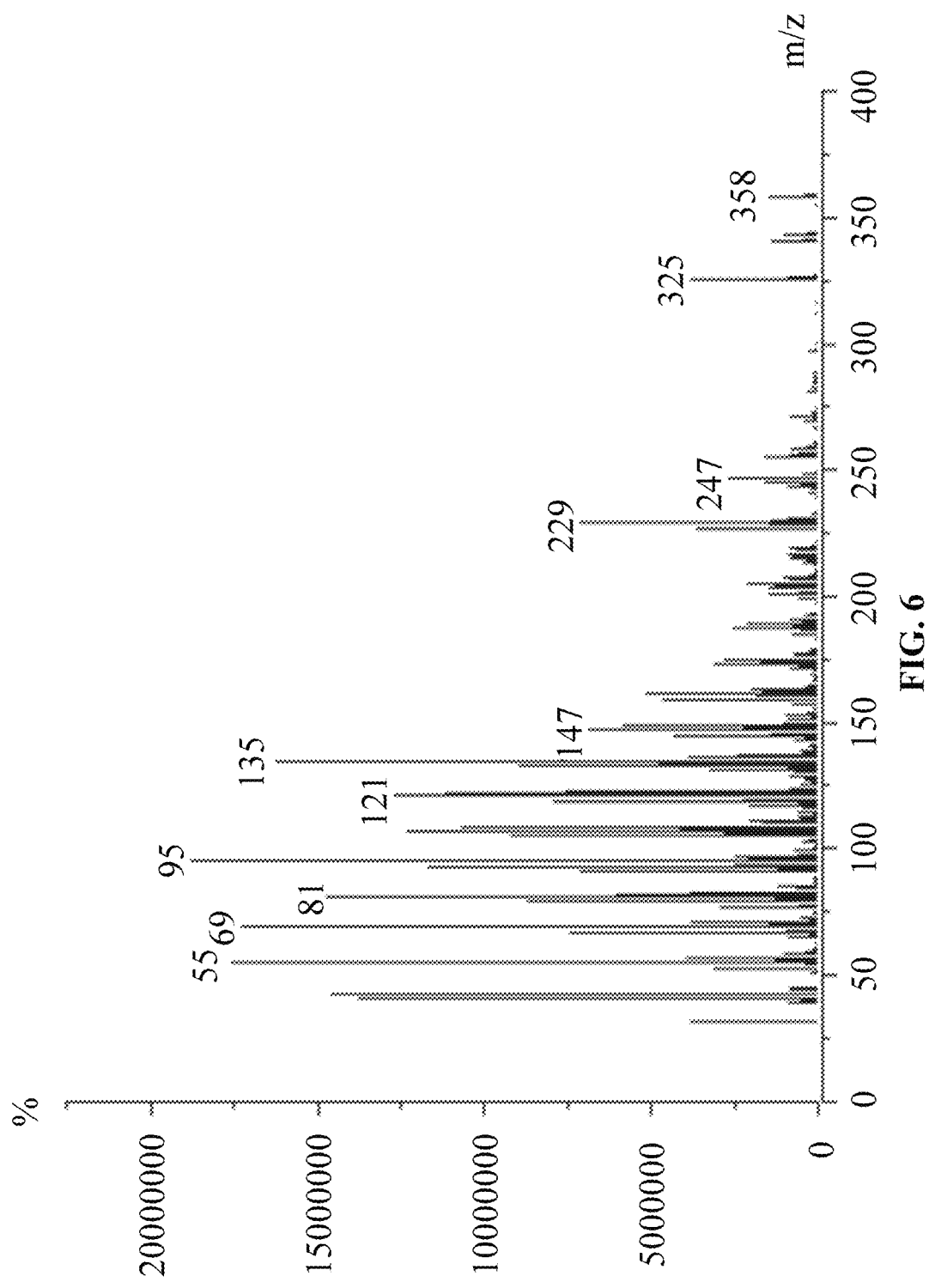
FIG. 6 is a mass spectrum of products of in vitro reaction using DMAPP and IPP as substrates.

To clarify the function of AuOS, four species of substrates of DMAPP (dimethylallyl diphosphate), GPP (geranyl diphosphate), FPP (farnesyl diphosphate), and GGPP (geranylgeranyl diphosphate), respectively, with added IPP (isopentenyl diphosphate) (chemicals from Sigma-Aldrich) were used in the reaction system (50 μL): 220 μM DMAPP (or GPP, FPP, GGPP), 340 μM IPP, 0.1 M Tris-HCl (pH 7.4), 2 mM DTT (dithiothreitol), 5 mM $MgCl_2$ and 9.4 μM AuOS, reacted at 30° C. for 3 h. After the reaction, the resultant was extracted using ethyl acetate at the same volume for 3 times, dried the organic solvent by organomation, and then dissolved using 50 μL ethyl acetate for GC-MS (GC-MS) detection. The results are as follows:

(1) Using DMAPP and IPP as substrates, according to the above in vitro reaction system, and as the above reaction product detection GC-MS method, the results are: ophiobolin core structure appeared at T=16.986 min on the chromatogram, and the mass charge ratios (m/z) characterized for ophiobolin core structure, such as: m/z=55, 69, 81, 95, 121, 135, 147, 229, 247, 325, 358 (Ryota Chiba, Atsushi Minami, Katsuya Gomi, et al. Identification of ophiobolin F synthase by a genome mining approach: a sesterterpene synthase from *Aspergillus clavatus*. Organic Letters. 2013, 15 (3), 594-597) appeared from the mass spectra. The chromatogram is showed in FIG. 5 and the mass spectrum is showed in FIG. 6.

Figure 7:
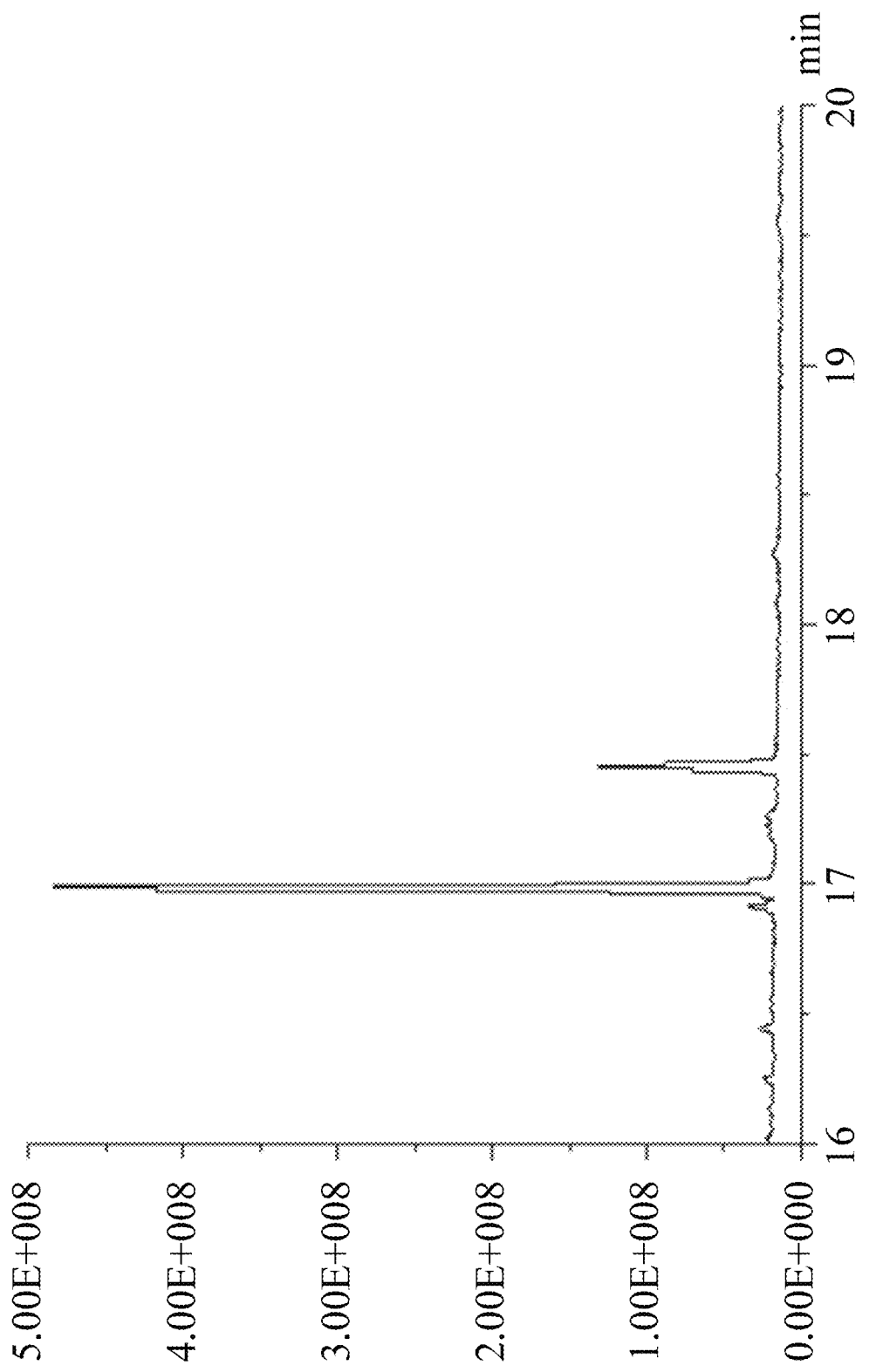
FIG. 7 is a chromatogram of products of in vitro reaction using FPP and IPP as substrates.
Figure 8:
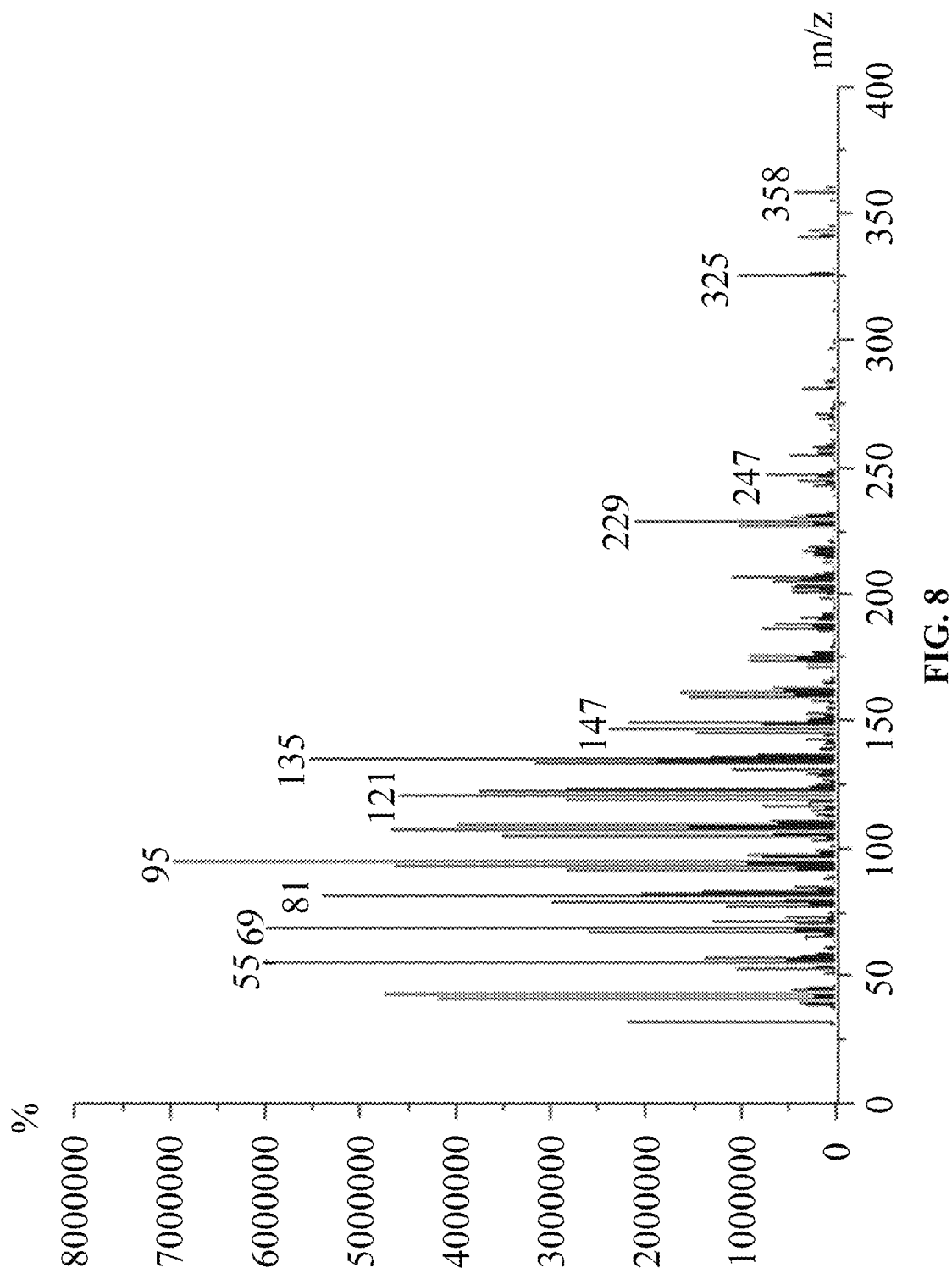
FIG. 8 is a mass spectrum of products of in vitro reaction using FPP and IPP as substrates.

(2) Using FPP and IPP as substrates, according to the above in vitro reaction system, and as the above reaction product detection GC-MS method, the results are: ophiobolin core structure appeared at T=16.986 min on the chromatogram, and the mass charge ratios (m/z) characterized for ophiobolin core structure, such as: m/z=55, 69, 81, 95, 121, 135, 147, 229, 247, 325, 358 (Ryota Chiba, Atsushi Minami, Katsuya Gomi, et al. Identification of ophiobolin F synthase by a genome mining approach: a sesterterpene synthase from *Aspergillus clavatus*. Organic Letters. 2013, 15 (3), 594-597) appeared from the mass spectra. The chromatogram is showed in FIG. 7 and the mass spectrum is showed in FIG. 8.

Figure 9:
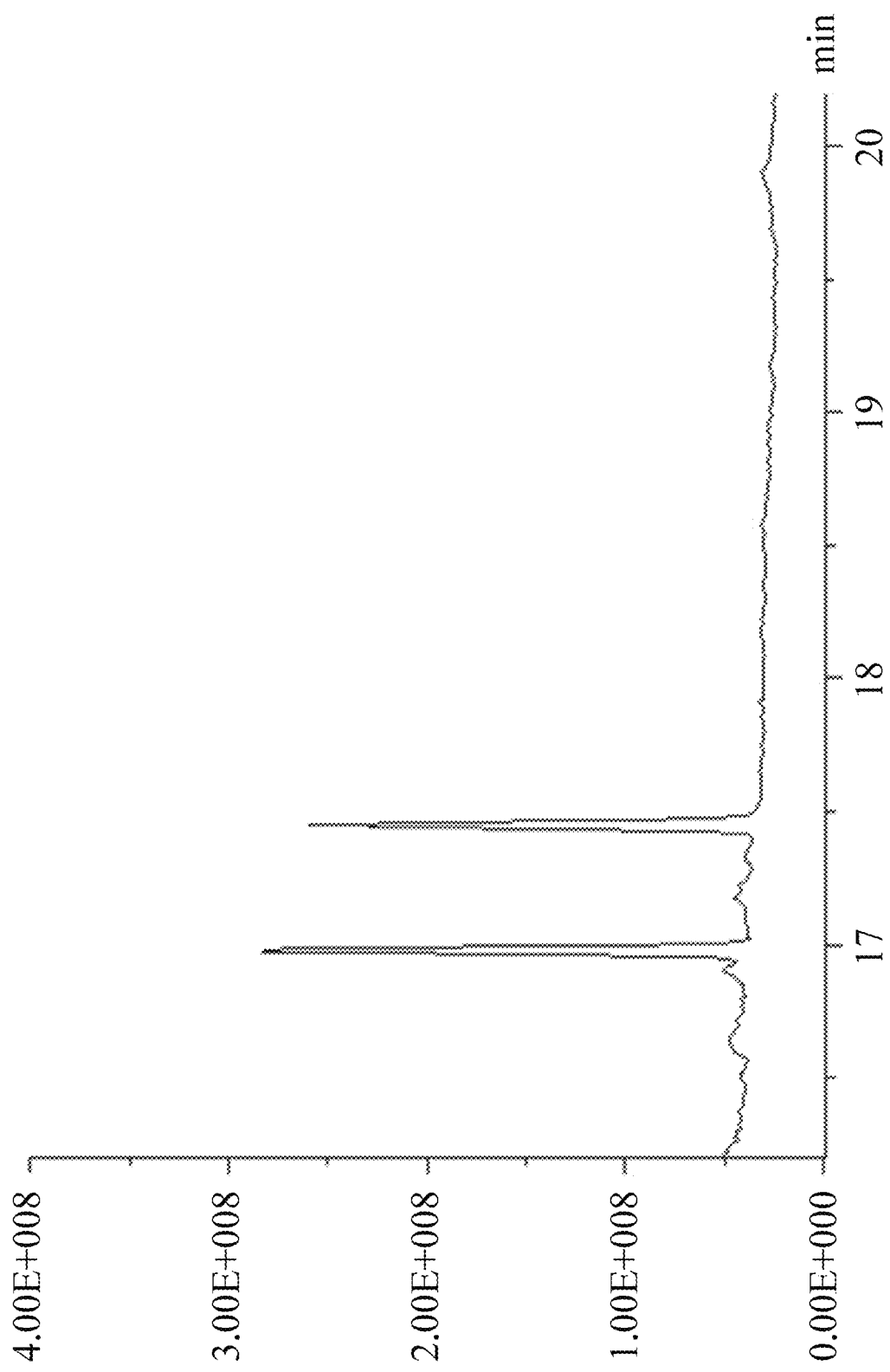
FIG. 9 is a chromatogram of products of in vitro reaction using GPP and IPP as substrates.
Figure 10:
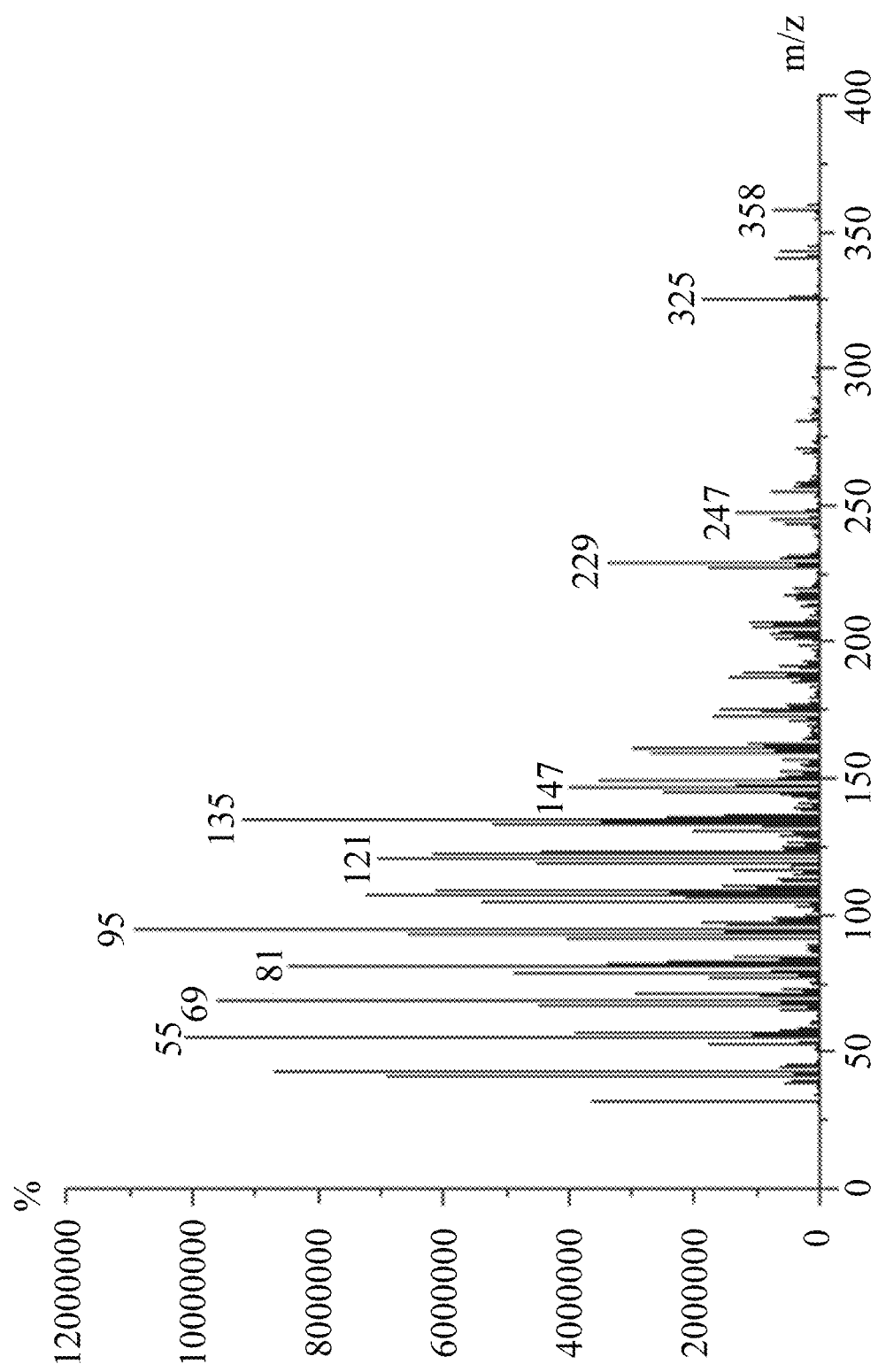
FIG. 10 is a mass spectrum of products of in vitro reaction using GPP and IPP as substrates.

(3) Using GPP and IPP as substrates, according to the above in vitro reaction system, and as the above reaction product detection GC-MS method, the results are: ophiobolin core structure appeared at T=16.986 min on the chromatogram, and the mass charge ratios (m/z) characterized for ophiobolin core structure, such as: m/z=55, 69, 81, 95, 121, 135, 147, 229, 247, 325, 358 (Ryota Chiba, Atsushi Minami, Katsuya Gomi, et al. Identification of ophiobolin F synthase by a genome mining approach: a sesterterpene synthase from *Aspergillus clavatus*. Organic Letters. 2013, 15 (3), 594-597) appeared from the mass spectra. The chromatogram is showed in FIG. 9 and the mass spectrum is showed in FIG. 10.

Figure 11:
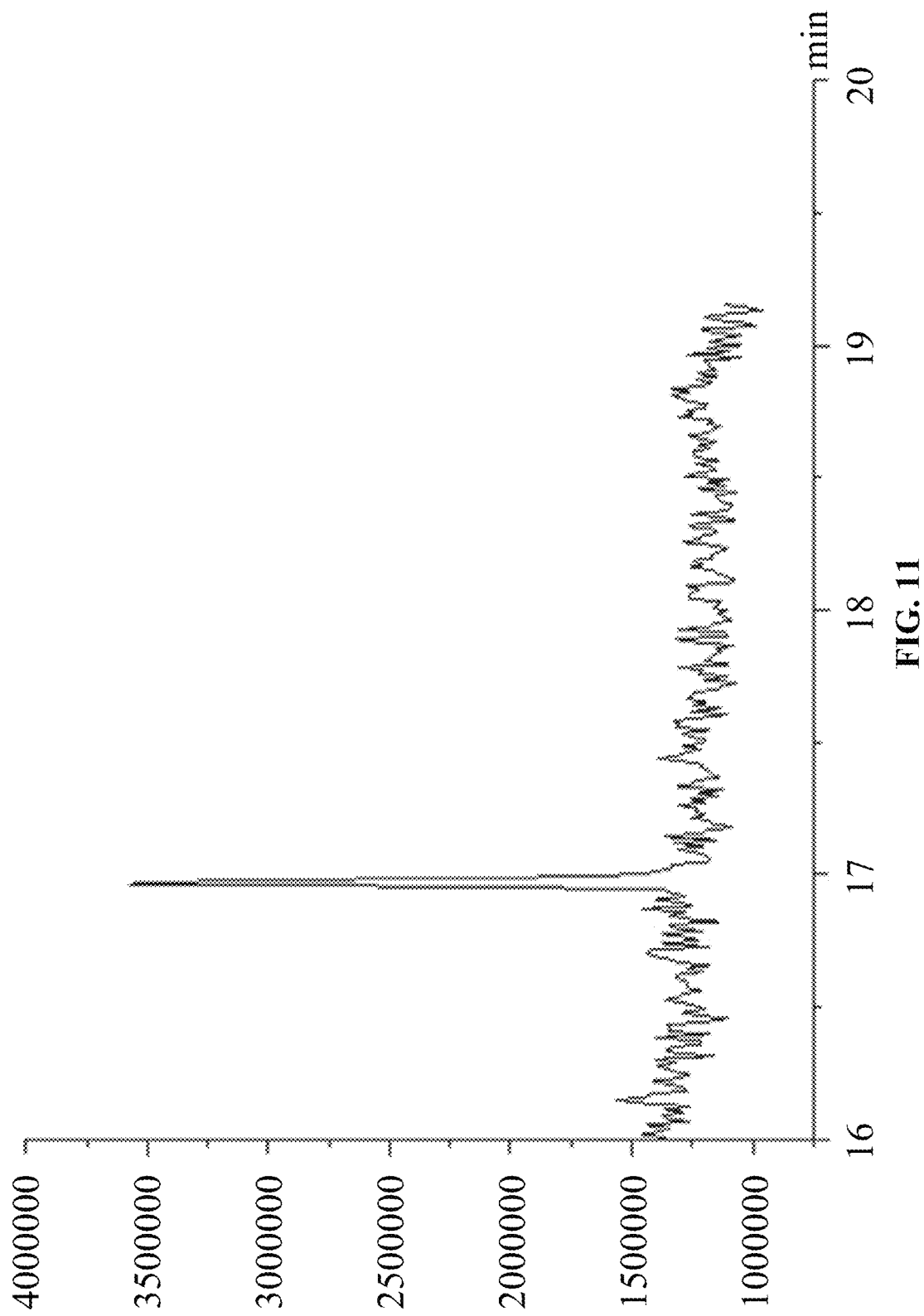
FIG. 11 is a chromatogram of products of in vitro reaction using GGPP and IPP as substrates.
Figure 12:
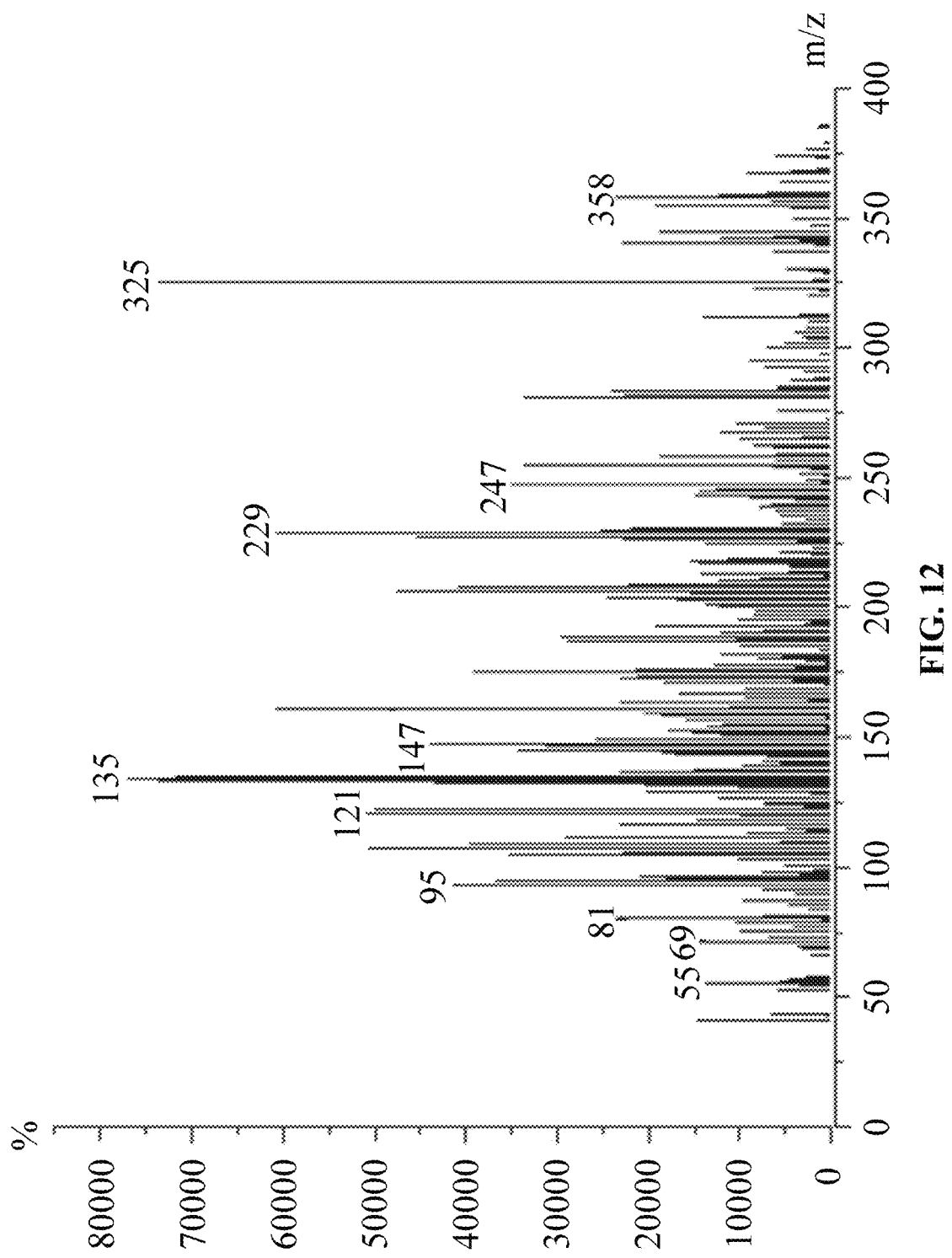
FIG. 12 is a mass spectrum of products of in vitro reaction using GGPP and IPP as substrates.

(4) Using GGPP and IPP as substrates, according to the above in vitro reaction system, and as the above reaction product detection GC-MS method, the results are: ophiobolin core structure appeared at T=16.986 min on the chromatogram, and the mass charge ratios (m/z) characterized for ophiobolin core structure, such as: m/z=55, 69, 81, 95, 121, 135, 147, 229, 247, 325, 358 (Ryota Chiba, Atsushi Minami, Katsuya Gomi, et al. Identification of ophiobolin F synthase by a genome mining approach: a sesterterpene synthase from *Aspergillus clavatus*. Organic Letters. 2013, 15 (3), 594-597) appeared from the mass spectra. The chromatogram is showed in FIG. 11 and the mass spectrum is showed in FIG. 12.

From the above results, AuOS protein can use four species of substrates of DMAPP, GPP, FPP and GGPP, respectively, added with IPP to biosynthesis the core structure of ophiobolin; also inferred that the protein can catalyze both chain elongation and terpene cyclation and carry the de novel biosynthesis of C5-C8-C5 structure from DMAPP.

Unless otherwise indicated, the numerical ranges involved in the invention include the end values. While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:

1. A cDNA, wherein the cDNA comprises the nucleic acid sequence of SEQ ID NO: 2.

2. A method for preparing an ophiobolin precursor, the method comprising:
   1) extracting RNA from mycelia of *Aspergillus* sp. 094102 which has been deposited in China Center for Type Culture Collection (CCTCC) with an accession number: CCTCC NO. M208153;
   2) reverse-transcribing the RNA of 1) into a cDNA;
   3) conducting PCR amplification of the cDNA of 2) with a pair of primers to obtain a PCR product mixture;
   4) recovering a target DNA fragment from the PCR product mixture of 3), wherein the target DNA fragment comprises the nucleic acid sequence of SEQ ID NO: 2 ligated to recognition sites of restriction enzymes Nde I and Hind III;
   5) ligating the target DNA fragment into a first vector to obtain a first recombinant plasmid;
   6) digesting the target DNA fragment from the first recombinant plasmid of 5) and inserting the target DNA fragment into a second vector to obtain a second recombinant plasmid;
   7) transforming the second recombinant plasmid of 6) into *Escherichia coli* BL21 to obtain an engineered *Escherichia coli* strain;
   8) cultivating the engineered *Escherichia coli* strain of 7) to obtain a target protein encoded by the target DNA fragment;
   9) purifying the target protein; and
   10) in vitro synthesizing an ophiobolin precursor from a first substrate and a second substrate using the target protein as a catalyst, wherein the first substrate is selected from dimethylallyl diphosphate, geranyl diphosphate, farnesyl diphosphate, and geranylgeranyl diphosphate, the second substrate is isopentenyl diphosphate, and the ophiobolin precursor has a molecular structure as follows:

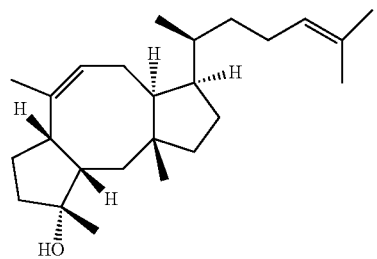 [SMILES: CC(C)=CCC[C@H](C)[C@H]1CC[C@]2(C)C[C@H]3[C@H](CC[C@@]3(C)O)/C(C)=C\C[C@@H]12]

3. The method of claim 2, wherein the pair of primers of 3) comprise the nucleic acid sequence of each of SEQ ID NO: 4 and SEQ ID NO: 5, respectively.

4. A recombinant plasmid, wherein:
   the engineered plasmid is a pET28a vector comprising a target DNA sequence; and
   the target DNA sequence comprises the nucleic acid sequence of SEQ ID NO: 2.

5. An engineered *Escherichia coli* strain, the engineered *Escherichia coli* strain comprising the recombinant plasmid of claim 4.

* * * * *

SEQUENCE LISTING

<160> NUMBER OF SEQ ID NOS: 5

<210> SEQ ID NO 1
<211> LENGTH: 2350
<212> TYPE: DNA
<213> ORGANISM: Artificial Sequence
<220> FEATURE:
<223> OTHER INFORMATION: Fully synthetic

<400> SEQUENCE: 1

| | | | | | |
|---|---|---|---|---|---|
| atggagtata | agtactcgac | catcgtcgac | agttccaagt | gggacccccga | gggcctgatc | 60 |
| gagggggatcc | ctctgcggaa | gcacgaagcc | ggggacctgg | aagaggtcgg | ttcgttccgg | 120 |
| gtccaggagg | actggcgccg | cctggtcggg | cccgtggaga | atccgttccg | gggctccctg | 180 |
| ggacccgaga | tcagtttcat | cacatacacc | gtgccgaat | gtttgccgga | gaggctagag | 240 |
| gccatcagct | atgggcttga | ctatggcttc | ctgcatgatg | gtatgtcatg | gttgctgctt | 300 |
| gcctgtgcgc | cgaacacgaa | agctaacccg | cccaccactc | attcttttag | acagatcga | 360 |
| cacgaaaatc | gaagaggccg | agctcgacga | cgtcggcgca | gccctggccc | agggcggatc | 420 |
| gaccggcaag | atccaagagg | ggaccaaatc | ctcggggaag | cgcaagatgg | ccgcgcagct | 480 |
| gctccgcgag | atgatggccc | tcgacccgga | gcgggccatg | acactggcca | agagttgggc | 540 |
| gcagggtgtg | cagcactcgg | ccagacgggt | ggaggagaag | gactggaagt | cgcttgacga | 600 |
| gtacatcccc | ttccggtgta | tggacctggg | gtacatgcac | tggcacgggc | tggtgacctt | 660 |
| tgggtgtgcg | attaccgtcc | ccgaggaaga | ggaggaggga | agacgacgc | tcctcgagcc | 720 |
| ggcggtgatt | gcgtgcctga | tgacgaatga | tctcttctcg | tacgaaaagg | agaagaacga | 780 |
| caataacccg | cagaacgcgg | tcgcggtcat | catgaaaatc | cacaagtgca | gtgaggagga | 840 |
| ggcacgagac | atttgcaagc | agcgcatccg | ccttgaatgc | cgcaagtatg | cccgcattgt | 900 |
| caaggagacg | ctcgcgagaa | cggatatttc | gctggacctg | aagaggtata | ttgagatcat | 960 |
| gcagtacacc | gtctctggca | actgggcctg | gagcacgcag | tgcccgaggt | accacgctga | 1020 |
| tgccaagttc | aacgaattgc | agatgctgag | ggcagagcat | ggggttgcaa | agtatcccgc | 1080 |
| gcgatattcg | ctagagaaca | ggaaaaacgg | cgccaacggg | gtcaacggtg | ttaatggcat | 1140 |
| taatggcgtc | aacggagtca | acggagtcaa | tggcaagaga | aaaagaagcg | agaagagac | 1200 |
| tgcagatgat | gcacgaacaa | acggcaatgg | gatcaagaaa | ccagcacatg | ttctcgagta | 1260 |
| cagggactca | ttagttcttg | aggatattgt | ggctctcagc | ctcgactgga | accttccaga | 1320 |
| cctgagcgat | ggcgtaagtt | ttccectctt | ctcttctgtc | gagactgtac | tgacagcatc | 1380 |
| ggatcaggtc | gtcgtccagc | cctacaaata | cctcacctcg | ctgccatcca | agggcttccg | 1440 |
| tgaccaggcg | atagactcgc | tcaacacatg | gctcagggtc | cccacaaaga | ccaccaagat | 1500 |
| gatcaaggac | gtgatcaaga | tgctgcacag | cgcctcgttg | atgtaagcac | atcctctgcc | 1560 |
| aacccatcct | ccctctaac | cctcccccag | gctcgacgac | atcgaagaca | actcgcctct | 1620 |
| ccgccgcggc | aagccctcca | cccacgtcat | ctacggcaac | gcccaaacca | tcaacagcgc | 1680 |
| cacataccaa | tacaccgaag | cgacaggcct | cgccgcccgc | ctcccaacc | cgacctccct | 1740 |
| gcgcatctac | ctcgaagaag | tccagcagct | gtacatcggc | cagagctacg | acctctactg | 1800 |
| gacgcacaac | gccctgtgcc | cgtccatccc | ggagtacctc | aagatggtcg | accaaaagac | 1860 |
| cggcgggctc | ttccgcatgc | tcacccgcct | gatggtctcc | gagagcccg | cgcgcagctc | 1920 |
| catcctcgac | cagaccctgt | acccgctgag | ccacctcatc | ggccgcttct | tccagatccg | 1980 |
| cgacgactat | cagaatctgg | cgtcggccga | gtatgcccgc | cagaagggggt | atgcggagga | 2040 |

-continued

| | |
|---|---|
| tctggacgag ggcaagtatt cgttcacgct gattcattgc atcaatacgc tcgaggcgga | 2100 |
| ggcttcgctg gcgagcgaga agatggcctt gcgcgcgttt ctgataaaga ggcgggtgga | 2160 |
| ttcgagtctg agtaatgagt cgaagcgcga ggtgttggat atcatgaaga agaccaagag | 2220 |
| cctggagtat accctggggg tgttgcgggc gttgcaggcg gagctcgaga aggaggtgga | 2280 |
| tagcctcgag gccaagtttg gcgaggagaa cttttcgctc aggatgatgc tggagctgct | 2340 |
| gaaggtttga | 2350 |

<210> SEQ ID NO 2
<211> LENGTH: 2178
<212> TYPE: DNA
<213> ORGANISM: Artificial Sequence
<220> FEATURE:
<223> OTHER INFORMATION: Fully synthetic

<400> SEQUENCE: 2

| | |
|---|---|
| atggagtata agtactcgac catcgtcgac agttccaagt gggaccccga gggcctgatc | 60 |
| gaggggatcc ctctgcggaa gcacgaagcc ggggacctgg aagaggtcgg ttcgttccgg | 120 |
| gtccaggagg actggcgccg cctggtcggg cccgtggaga atccgttccg gggctccctg | 180 |
| ggacccgaga tcagtttcat cacatacacc gtgccggaat gtttgccgga gaggctagag | 240 |
| gccatcagct atgggcttga ctatggcttc ctgcatgatg acgagatcga cacgaaaatc | 300 |
| gaagaggccg agctcgacga cgtcggcgca gccctggccc agggcggatc gaccggcaag | 360 |
| atccaagagg ggaccaaatc ctcggggaag cgcaagatgg ccgcgcagct gctccgcgag | 420 |
| atgatggccc tcgacccgga gcgggccatg acactggcca agagttgggc gcagggtgtg | 480 |
| cagcactcgg ccagacgggt ggaggagaag gactggaagt cgcttgacga gtacatcccc | 540 |
| ttccggtgta tggacctggg gtacatgcac tggcacgggc tggtgacctt tgggtgtgcg | 600 |
| attaccgtcc ccgaggaaga ggaggaggag agacggacgc tcctcgagcc ggcggtgatt | 660 |
| gcgtgcctga tgacgaatga tctcttctcg tacgaaaagg agaagaacga caataacccg | 720 |
| cagaacgcgg tcgcggtcat catgaaaaatc cacaagtgca gtgaggagga ggcacgagac | 780 |
| atttgcaagc agcgcatccg ccttgaatgc cgcaagtatg cccgcattgt caaggagacg | 840 |
| ctcgcgagaa cggatatttc gctggacctg aagaggtata ttgagatcat gcagtacacc | 900 |
| gtctctggca actgggcctg gagcacgcag tgcccgaggt accacgctga tgccaagttc | 960 |
| aacgaattgc agatgctgag ggcagagcat ggggttgcaa agtatcccgc gcgatattcg | 1020 |
| ctagagaaca ggaaaaacgg cgccaacggg gtcaacggtg ttaatggcat taatggcgtc | 1080 |
| aacggagtca acggagtcaa tggcaagaga aaaagaagcg gagaagagac tgcagatgat | 1140 |
| gcacgaacaa acggcaatgg gatcaagaaa ccagcacatg ttctcgagta cagggactca | 1200 |
| ttagttcttg aggatattgt ggctctcagc ctcgactgga accttccaga cctgagcgat | 1260 |
| ggcgtcgtcg tccagcccta caaatacctc acctcgctgc catccaaggg cttccgtgac | 1320 |
| caggcgatag actcgctcaa cacatggctc agggtcccca caaagaccac caagatgatc | 1380 |
| aaggacgtga tcaagatgct gcacagcgcc tcgttgatgc tcgacgacat cgaagacaac | 1440 |
| tcgcctctcc gccgcggcaa gccctccacc cacgtcatct acggcaacgc ccaaaccatc | 1500 |
| aacagcgcca cataccaata caccgaagcg acaggcctcg ccgcccgcct cccccaaccc g | 1560 |
| acctccctgc gcatctacct cgaagaagtc cagcagctgt acatcggcca gagctacgac | 1620 |
| ctctactgga cgcacaacgc cctgtgcccg tccatcccgg agtacctcaa gatggtcgac | 1680 |

-continued

```
caaaagaccg gcgggctctt ccgcatgctc acccgcctga tggtctccga gagccccgcg    1740
cgcagctcca tcctcgacca gaccctgtac ccgctgagcc acctcatcgg ccgcttcttc    1800
cagatccgcg acgactatca gaatctggcg tcggccgagt atgcccgcca aaggggtat    1860 gcggaggatc tggacgaggg caagtattcg ttcacgctga ttcattgcat caatacgctc    1920
gaggcggagg cttcgctggc gagcgagaag atggccttgc gcgcgtttct gataaagagg    1980
cgggtggatt cgagtctgag taatgagtcg aagcgcgagg tgttggatat catgaagaag    2040
accaagagcc tggagtatac cctgggggtg ttgcgggcgt tgcaggcgga gctcgagaag    2100
gaggtggata gcctcgaggc caagtttggc gaggagaact tttcgctcag gatgatgctg    2160
gagctgctga aggtttga                                                  2178
```

<210> SEQ ID NO 3
<211> LENGTH: 725
<212> TYPE: PRT
<213> ORGANISM: Artificial Sequence
<220> FEATURE:
<223> OTHER INFORMATION: Fully synthetic

<400> SEQUENCE: 3

```
Met Glu Tyr Lys Tyr Ser Thr Ile Val Asp Ser Ser Lys Trp Asp Pro
1               5                   10                  15

Glu Gly Leu Ile Glu Gly Ile Pro Leu Arg Lys His Glu Ala Gly Asp
            20                  25                  30

Leu Glu Glu Val Gly Ser Phe Arg Val Gln Glu Asp Trp Arg Arg Leu
        35                  40                  45

Val Gly Pro Val Glu Asn Pro Phe Arg Gly Ser Leu Gly Pro Glu Ile
    50                  55                  60

Ser Phe Ile Thr Tyr Thr Val Pro Glu Cys Leu Pro Glu Arg Leu Glu
65                  70                  75                  80

Ala Ile Ser Tyr Gly Leu Asp Tyr Gly Phe Leu His Asp Asp Glu Ile
                85                  90                  95

Asp Thr Lys Ile Glu Glu Ala Glu Leu Asp Asp Val Gly Ala Ala Leu
            100                 105                 110

Ala Gln Gly Gly Ser Thr Gly Lys Ile Gln Glu Gly Thr Lys Ser Ser
        115                 120                 125

Gly Lys Arg Lys Met Ala Ala Gln Leu Leu Arg Glu Met Met Ala Leu
130                 135                 140

Asp Pro Glu Arg Ala Met Thr Leu Ala Lys Ser Trp Ala Gln Gly Val
145                 150                 155                 160

Gln His Ser Ala Arg Arg Val Glu Glu Lys Asp Trp Lys Ser Leu Asp
                165                 170                 175

Glu Tyr Ile Pro Phe Arg Cys Met Asp Leu Gly Tyr Met His Trp His
            180                 185                 190

Gly Leu Val Thr Phe Gly Cys Ala Ile Thr Val Pro Glu Glu Glu Glu
        195                 200                 205

Glu Glu Arg Arg Thr Leu Leu Glu Pro Ala Val Ile Ala Cys Leu Met
    210                 215                 220

Thr Asn Asp Leu Phe Ser Tyr Glu Lys Glu Lys Asn Asp Asn Asn Pro
225                 230                 235                 240

Gln Asn Ala Val Ala Val Ile Met Lys Ile His Lys Cys Ser Glu Glu
                245                 250                 255

Glu Ala Arg Asp Ile Cys Lys Gln Arg Ile Arg Leu Gly Cys Arg Lys
            260                 265                 270
```

```
Tyr Ala Arg Ile Val Lys Glu Thr Leu Ala Arg Thr Asp Ile Ser Leu
            275                 280                 285

Asp Leu Lys Arg Tyr Ile Glu Ile Met Gln Tyr Thr Val Ser Gly Asn
290                 295                 300

Trp Ala Trp Ser Thr Gln Cys Pro Arg Tyr His Ala Asp Ala Lys Phe
305                 310                 315                 320

Asn Glu Leu Gln Met Leu Arg Ala Glu His Gly Val Ala Lys Tyr Pro
                325                 330                 335

Ala Arg Tyr Ser Leu Glu Asn Arg Lys Asn Gly Ala Asn Gly Val Asn
            340                 345                 350

Gly Val Asn Gly Ile Asn Gly Val Asn Gly Val Asn Gly Val Asn Gly
            355                 360                 365

Lys Arg Lys Arg Ser Gly Glu Glu Thr Ala Asp Asp Ala Arg Thr Asn
370                 375                 380

Gly Asn Gly Ile Lys Lys Pro Ala His Val Leu Glu Tyr Arg Asp Ser
385                 390                 395                 400

Leu Val Leu Glu Asp Ile Val Ala Leu Ser Leu Asp Trp Asn Leu Pro
                405                 410                 415

Asp Leu Ser Asp Gly Val Val Gln Pro Tyr Lys Tyr Leu Thr Ser
                420                 425                 430

Leu Pro Ser Lys Gly Phe Arg Asp Gln Ala Ile Asp Ser Leu Asn Thr
            435                 440                 445

Trp Leu Arg Val Pro Thr Lys Thr Thr Lys Met Ile Lys Asp Val Ile
            450                 455                 460

Lys Met Leu His Ser Ala Ser Leu Met Leu Asp Asp Ile Glu Asp Asn
465                 470                 475                 480

Ser Pro Leu Arg Arg Gly Lys Pro Ser Thr His Val Ile Tyr Gly Asn
                485                 490                 495

Ala Gln Thr Ile Asn Ser Ala Thr Tyr Gln Tyr Thr Glu Ala Thr Gly
            500                 505                 510

Leu Ala Ala Arg Leu Pro Asn Pro Thr Ser Leu Arg Ile Tyr Leu Glu
            515                 520                 525

Glu Val Gln Gln Leu Tyr Ile Gly Gln Ser Tyr Asp Leu Tyr Trp Thr
            530                 535                 540

His Asn Ala Leu Cys Pro Ser Ile Pro Glu Tyr Leu Lys Met Val Asp
545                 550                 555                 560

Gln Lys Thr Gly Gly Leu Phe Arg Met Leu Thr Arg Leu Met Val Ser
                565                 570                 575

Glu Ser Pro Ala Arg Ser Ser Ile Leu Asp Gln Thr Leu Tyr Pro Leu
            580                 585                 590

Ser His Leu Ile Gly Arg Phe Phe Gln Ile Arg Asp Asp Tyr Gln Asn
            595                 600                 605

Leu Ala Ser Ala Glu Tyr Ala Arg Gln Lys Gly Tyr Ala Glu Asp Leu
610                 615                 620

Asp Glu Gly Lys Tyr Ser Phe Thr Leu Ile His Cys Ile Asn Thr Leu
625                 630                 635                 640

Glu Ala Glu Ala Ser Leu Ala Ser Glu Lys Met Ala Leu Arg Ala Phe
                645                 650                 655

Leu Ile Lys Arg Arg Val Asp Ser Leu Ser Asn Glu Ser Lys Arg
            660                 665                 670

Glu Val Leu Asp Ile Met Lys Lys Thr Lys Ser Leu Glu Tyr Thr Leu
            675                 680                 685

Gly Val Leu Arg Ala Leu Gln Ala Glu Leu Glu Lys Glu Val Asp Ser
```

```
                690              695              700
Leu Glu Ala Lys Phe Gly Glu Glu Asn Phe Ser Leu Arg Met Met Leu
705                     710                 715                 720

Glu Leu Leu Lys Val
                725

<210> SEQ ID NO 4
<211> LENGTH: 27
<212> TYPE: DNA
<213> ORGANISM: Artificial Sequence
<220> FEATURE:
<223> OTHER INFORMATION: Fully synthetic

<400> SEQUENCE: 4
catatgatgg agtataagta ctcgacc                                          27

<210> SEQ ID NO 5
<211> LENGTH: 26
<212> TYPE: DNA
<213> ORGANISM: Artificial Sequence
<220> FEATURE:
<223> OTHER INFORMATION: Fully synthetic

<400> SEQUENCE: 5
aagctttcaa accttcagca gctcca                                           26
```